United States Patent
Winchester, Jr. et al.

(10) Patent No.: US 7,113,817 B1
(45) Date of Patent: Sep. 26, 2006

(54) OPTICAL IMAGING OF BLOOD CIRCULATION VELOCITIES

(75) Inventors: Leonard W. Winchester, Jr., Yorktown, VA (US); Nee-Yin Chou, Yorktown, VA (US)

(73) Assignee: WinTec, LLC, Yorktown, VA (US)

( * ) Notice: Subject to any disclaimer, the term of this patent is extended or adjusted under 35 U.S.C. 154(b) by 402 days.

(21) Appl. No.: 09/969,660

(22) Filed: Oct. 4, 2001

(51) Int. Cl.
*A61B 6/00* (2006.01)

(52) U.S. Cl. ............ 600/476; 600/477; 600/478; 600/473; 128/668; 356/27; 356/58; 382/107; 382/134; 73/342

(58) Field of Classification Search ........... 600/473, 600/476, 479, 504, 363, 407, 310
See application file for complete search history.

(56) References Cited

U.S. PATENT DOCUMENTS

| | | | | |
|---|---|---|---|---|
| 4,030,888 A * | 6/1977 | Yamamoto et al. | ......... | 422/67 |
| 4,746,211 A * | 5/1988 | Ruth et al. | ......... | 356/28.5 |
| 4,952,050 A * | 8/1990 | Aizu et al. | ......... | 351/221 |
| 4,979,818 A * | 12/1990 | Kobayashi | ......... | 356/28 |
| 5,240,006 A * | 8/1993 | Fujii et al. | ......... | 600/425 |
| 5,291,886 A * | 3/1994 | Katayama et al. | ......... | 600/310 |
| 5,339,817 A * | 8/1994 | Nilsson | ......... | 600/473 |
| 5,598,841 A * | 2/1997 | Taniji et al. | ......... | 600/342 |
| 5,865,738 A * | 2/1999 | Morcos et al. | ......... | 600/365 |
| 5,954,658 A * | 9/1999 | Gorti | ......... | 600/504 |
| 6,006,128 A * | 12/1999 | Izatt et al. | ......... | 600/476 |
| 6,045,511 A * | 4/2000 | Ott et al. | ......... | 600/504 |
| 6,173,197 B1* | 1/2001 | Boggett et al. | ......... | 600/310 |
| 6,263,227 B1* | 7/2001 | Boggett et al. | ......... | 600/407 |
| 6,549,801 B1* | 4/2003 | Chen et al. | ......... | 600/425 |

* cited by examiner

*Primary Examiner*—Eleni Mantis-Mercader
*Assistant Examiner*—William C. Jung
(74) *Attorney, Agent, or Firm*—James Creighton Wray

(57) ABSTRACT

New devices and methods are provided for noninvasive and noncontact real-time measurements of tissue blood velocity. The invention uses a digital imaging device such as a detector array that allows independent intensity measurements at each pixel to capture images of laser speckle patterns on any surfaces, such as tissue surfaces. The laser speckle is generated by illuminating the surface of interest with an expanded beam from a laser source such as a laser diode or a HeNe laser as long as the detector can detect that particular laser radiation. Digitized speckle images are analyzed using new algorithms for tissue optics and blood optics employing multiple scattering analysis and laser Doppler velocimetry analysis. The resultant two-dimensional images can be displayed on a color monitor and superimposed on images of the tissues.

30 Claims, 9 Drawing Sheets

- Light Skin
- ○ Dark Skin

OPTICAL IMAGING OF BLOOD CIRCULATION VELOCITIES

BACKGROUND OF THE INVENTION

The invention relates to sensing blood velocity in tissues such as skin, skin flaps, transplants, breasts, retinas, and internal organs and tissue.

The evaluation of hemodynamics is an important diagnostic subject and has been one of the most difficult challenges in medicine. In skin studies it is important to assess blood velocities over wide areas to determine blood perfusion and predict tissue viability. For surgical procedures involving skin flaps, a reliable method of quantitatively monitoring tissue blood velocity can provide predictive value in assessing tissue conditions during partial detachments and before, during, and after reattachment to avoid tissue necrosis. The same is true in the transplant of tissues and organs and before, during, and following surgery.

The invention is also useful in diagnosing tissue damage due to complications of diabetes, addressing practicality and viability of tissue repairs and vascular densities, and angiogenesis in large sites being studied for possible carcinomas, for example, breast cancer.

It is important to assess blood perfusion and velocities over large areas in real-time and to be able to provide the information to attending medical personnel in manners that are readily perceivable and understandable.

The invention is useful for assessing surgical procedures such as reconstructive surgery involving flaps, the treatment of vascular diseases, the condition of diabetic complications, and the progression of tumors. It can be used to monitor the status of surgically implanted flaps.

Free tissue transfer is a routine surgical procedure with a success rate of up to 95%. Complications generally occur within 48 hours of the initial surgery. Tissue necrosis sets in if poor tissue perfusion is not corrected within 12 hours of surgery. The need for early detection of vascular insufficiency in free flaps is important as the success of corrective surgery strongly depends on the time elapsed since the onset of vascular insufficiency. Between 12 and 17% of flap surgery cases require re-exploration due to post-operative vascular complications that threaten flap viability. Flap salvage rates can be as high as 50%, depending on the procedure and the elapsed time since the onset of vascular occlusion.

Flap viability can be assessed by clinical observations of flap color, tissue turgor, capillary refill, and bleeding after a pinprick, and using monitoring techniques such as laser Doppler velocimetry, differential thermometry, transcutaneous oxygen measurement, plethysmography, and Doppler ultrasound. Clinical visual observation remains the most popular means of assessing tissue viability. Early detection of decreased blood supply to the flap can be detected and corrective action can be taken in time to prevent wide-scale tissue necrosis and possibly eliminate the need for additional surgical procedures.

In the U.S., the breast cancer mortality rate is about 26 per hundred thousand women and the number of deaths due to breast cancer was nearly 44,000 in 1998. Early detection of breast tumors provides a better chance for breast conservation treatment and increases the survival rate. Current methods for detecting breast cancer are based primarily on physical examination and conventional mammography. The invention does not replace mammography as a primary breast tumor screening tool, however, it may serve as an adjunct tool that is economical and portable, and can be used by primary care physicians and gynecologists. It can be used to measure human breasts to estimate subcutaneous blood velocities of normal and diseased breast tissue. The differences between measurements of normal breasts, breasts with benign tumors, and breasts with malignant tumors can be quantified and used to assess the health of the breast.

Measurement of retinal blood velocities is an important application of the invention.

For example, the retina provides direct optical access to both the central nervous system (CNS) and afferent and efferent CNS vasculature. This unique feature has provided generations of ophthalmologists with the ability to evaluate multi-system diseases without invasive diagnostic testing using direct ophthalmoscopy, indirect ophthalmoscopy, and slit lamp biomicroscope examination utilizing 90 or 78 diopter lenses, and the Hruby lens. These methods, however, cannot directly quantify retinal blood velocity, nor do they detect preclinical alterations predictive of eventual significant morbidity. This is particularly pertinent to the insidious onset of glaucoma and macular degeneration. The trend toward preventive medicine prescribes a more sensitive technique to reliably quantify subtle changes in retinal hemodynamics.

Both incoherent and coherent optical techniques have been used to assess microcirculation. The incoherent approach includes the fluorescein dye dilution method and the blue field entoptic method for retinal blood velocity measurement, and plethysmography. The coherent approach is represented by the laser Doppler method and the dynamic laser speckle method. The former employs a focused laser beam to measure the frequency shifts of radiation scattered by a scatterer. It requires a scanning mechanism for imaging applications. Its application to turbid media requires a consideration of multiple scattering effect. The dynamic laser speckle technique has been used for both point measurements and imaging applications in cases where multiple scattering is not prominent, e.g., in monitoring blood and lymph flow in microvessels and in visualizing retinal microcirculation. Taking advantage of the advanced digital photography, the Laser Speckle Contrast Analysis (LSCA) technique extends the conventional laser speckle method to a nonscanning, full-field technique.

Needs exist for improved real-time measurement and display of blood perfusion and velocities. The needs are especially important in skin, skin flaps, surgical sites, transplants, breasts, and retinas, for example.

SUMMARY OF THE INVENTION

The invention extends the LSCA analysis to include multiple scattering (MS). The accuracy of the LSCA/MS technique is better than that of laser Doppler method. The invention provides an image sensor for measuring blood velocity and a means to assess tissue perfusion for monitoring conditions such as tissue necrosis, vascular insufficiency, cancer, macular degeneration, glaucoma, etc.

The difference between this invention and most speckle imaging techniques used by others is that the new method employs spatial averaging of the temporal measurements, whereas the temporal observation of the dynamic events was utilized by others. The fundamental difference between this invention and the LSCA method is the inclusion of multiple scattering into data analysis. This invention can be used to provide real-time, noninvasive, and quantitative monitoring of blood velocity. The blood velocity information can be overlaid onto a tissue image using a multicolored mapping technique and displayed in near real-time.

Both laser speckle velocimetry (LSV) and laser Doppler velocimetry (LDV) are based on the interference between the Doppler-shifted radiation scattered by red blood cells (RBCs) and the unshifted radiation scattered by tissue. The convoluted nature of the capillaries makes the direct measurement of RBC velocity difficult. The laser speckle pattern depends on the variation of surface roughness and the velocity distribution of moving particles (i.e., RBCs). Methods for determining velocity from laser speckle include the correlation of the power spectrum of speckle intensity, double-exposure photography, and laser speckle contrast analysis (LSCA). These methods differ in their applications, analysis, hardware requirements, and experimental procedures, and are essentially equivalent to LDV and photon correlation spectroscopy. The power spectrum method is the most frequently used LSV method for analyzing retinal blood velocity measurements, using a single scattering approximation to avoid the complexity of multiple scattering. The double-exposure photography uses a double-pulsed laser to illuminate a scattering volume and records the event on an analog medium, e.g., a photographic film.

The single-exposure photography uses spatial averaging of the temporal measurements—instead of monitoring speckle intensity in a time domain, one photographs the speckle pattern with a finite exposure time and examines spatial distribution of the intensity fluctuation time-averaged over the exposure time. It relies on the first-order statistics of the intensity, i.e., speckle contrast.

The invention combines digital and single-exposure photography to obtain velocity estimates over large sensing areas. Since it utilizes spatial averaging, it loses spatial resolution as compared with the LDV method. However, the spatial resolution can be improved by increasing optical magnification of the imaging system and/or by using a detector array such as a charged-couple device with small pixel size. This invention has the advantage of being a fill-field method that provides a global picture of the velocity pattern without the need for scanning or contact with the sampled tissue.

Mathematical Relations

Laser speckle is a random phenomenon that can only be described statistically by first considering a plane illuminated by a coherent electromagnetic wave of wavelength $\lambda$. The circular cross-section of the beam, i.e., the illuminated area of the plane, is characterized by $|x'|<a, |y'|<a$, and $z'=0$, where a is a length parameter. The intensity E at a point (x, y, z) is given by $$E(x, y, z) = \frac{1}{\lambda R_0}\left(\frac{z}{R_0}\right)\exp(-ikR_0)\int_0^a\int_0^a E(x', y', 0)\exp\left(ik\frac{xx' + yy'}{R_0}\right)dx'\,dy' \quad (1)$$

where k is the wave vector ($k=2\pi/\lambda$) and $R_o$ is the distance from the center of the circle to the viewing location, $R_o = (x^2+y^2+z^2)^{1/2}$. If a diffuser is placed in front of the incident beam, Eq. (1) becomes $$E(x,y,0)=\exp[-ikh(x,y)] \quad (2)$$

where h(x, y) describes the fine scale roughness or the velocity of particles passing through a point (x, y, 0). The phase fluctuation due to h(x, y) is superimposed on the resultant electric field, causing laser speckle. Spatial distribution of the digitized image is obtained by computing the average intensity <I(x,y)> over the square neighborhood of a point (x, y) of interest. The speckle contrast d(x, y) is defined by $$d(x, y) = \frac{\sigma(x, y)}{<I(x, y)>} \quad (3)$$

where $\sigma(x, y)$ is the standard deviation of intensity over the square neighborhood. The intensity averaging process removes background contributions from surface roughness. Both d and $\sigma$ depend on the statistics of blood velocity distribution and are affected by the presence of multiple scattering. Spatial properties of the time-averaged speckle pattern are equivalent to the temporal properties of the same pattern. The variance $\sigma^2$ of the spatial intensity variations equals the time average of the autocovariance $C_V(\tau)$ of the intensity fluctuations, $$\sigma^2(T) = \frac{1}{T}\int_0^T C_V(\tau)d\tau = \frac{1}{T}\int_0^T <[I(t)-<I>][I(t+\tau)-<I>]>d\tau \quad (4)$$

where T is the integration time.

For a stationary process, $C_V(\tau)$ can be written as $$C_V(\tau) = <I>^2 C_I^2(\tau) \quad (5)$$

where $C_I(\tau)$ is the autocorrelation function. Using single scattering approximation, $C_I(\tau)$ is expressed as a smooth negative exponential function, $C_I(\tau)=\exp(-\tau/\tau_c)$, where $\tau_c$ is the correlation time. The speckle contrast d at any point (x, y) in a pattern integrated over time T is written as $$d(x, y) = \left[\frac{\tau_c}{2T}(1 - \exp(-2T/\tau_c))\right]^{1/2} \quad (6)$$

Assuming that the characteristic (i.e., average) velocity $V_c$ is related to $\tau_c$ ($V_c=\mu(2\pi\tau_c)^{-1}$), Eq. (6) can be solved for $\tau_c$ using d and T. The value of $V_c$ can then be computed. Both the LDV and the LSCA methods measure $V_c$ which is the average of the radial component (along the direction toward the detector) of all illuminated particles in the detector field of view, $$V_c = \int_0^\infty Vg(V)dV \quad (7)$$

where g(V) is the assumed velocity distribution. Both Lorentzian and Maxwellian distributions have been used to describe the velocity distribution of RBCs. The distribution of velocities leads to "Doppler-broadening" of the frequency distribution of the scattered light.

In LDV, the frequency difference of the incident and scattered light is given by $\Delta f=v_l(f/c)$, where $v_l$ is the longitudinal component of the velocity, c is the speed of light, and $\theta$ is the frequency of the incident radiation. Multiple scattering from flowing blood cells and stationary tissue complicates the procedure for retrieving blood velocity parameters from intensity fluctuations. Evolution of the phase difference of the scattered light can be treated as a series of scattering events. The $\Delta f$ is a linear function of the particle velocity and has its origin in the Doppler effect. The mean $\Delta f$ of photons emerging from tissue can be calculated by integrating the scattering intensity over all possible events. The expression for $C_t(\tau)$ can be written as, $$C_t(\tau)=1+\beta(\exp(2m[I_i(\tau)-1])-\exp(-2m)) \quad (8)$$

where $\beta$ is the optical coherence of the signal at the viewing position, m is the average number of collisions the photon undergoes with a moving particle, and $I_i(\tau)$ is an intermediate scattering function defined by $$I_i(\tau) = \frac{\int_{-\pi}^{\pi} S(|Q(\theta)|) <\exp[iQ(\theta)\cdot\Delta R(\tau)]> \sin\theta\, d\theta}{\int_{-\pi}^{\pi} S(|Q(\theta)|)\sin\theta\, d\theta} \quad (9)$$

where $\Delta R(\tau)$ is the displacement of the center of mass of the moving particle during time $\tau$, $\theta$ is the scattering angle, $Q(\theta)$ is the Bragg scattering vector, and $S(Q(\theta).)$ is the structure factor of the average scatterer. $Q(\theta)$ can be written as $$Q(\theta) = |Q(\theta)| = \frac{4\pi n}{\lambda}\sin(\theta/2) \quad (10)$$

where n is the refractive index of the moving particle at $\lambda$. $S(Q(\theta).)$ can be approximated using the Rayleigh-Gans theory, $$S(Q) = \left[\frac{3}{(Qa)^3}(\sin(Qa) - \cos(Qa))\right]^2 \quad (11)$$

where a is the effective radius (2.75 μm) of the RBC.

Treatment of Multiple Scattering

The invention incorporates multiple scattering considerations into data analysis by calculating d (Eq. 3) using σ obtained from $\sigma^2$ (Eq. 4), and evaluating $C_t(\tau)$ (Eq. 8). Both $\beta$ and m can be obtained from an examination of the scattering process. A Monte Carlo program can be used to evaluate the average number of scattering events of the RBCs for any given laser wavelength and power density. The expectation value $<\exp(iQ(\theta)\cdot\Delta R(\tau))>$ is an ensemble average taken over all possible scattering events and must be averaged over a range of scattering angles and RBC velocities. The parameter $Q(\theta)$ appears in the numerator and the denominator of Eq. (9). It depends on the shape and relative size (as compared with $\lambda$) of the RBCs.

The computation process includes:

(1) Calculate the speckle contrast d for each pixel by computing the average intensity I and the standard deviation of intensity σ in a square neighborhood (e.g., a 7-pixel×7-pixel neighborhood). Assign this d value to the central point of the neighborhood. Repeat the process for every point in the array.

(2) Compute the characteristic velocity $V_c$ for each pixel using Eqs. (3), (4), and (8).

(3) Create visual output using color-coded images.

Theoretically, both LSCA and LDV yield the same results since they examine the interferometric patterns of the same phenomenon—frequency shift of light scattered by moving particles. The LSCA method applies the ergodic hypothesis, equivalence of spatial averaging and time averaging, to obtain speckle contrast and velocity. It averages velocity over a larger (e.g., 49-fold for a 7-pixel×7-pixel neighborhood) area than that of the single-pixel, time-dependent method, or the thin fiber Laser Doppler probe.

The invention reduces the effect of local tissue irregularities, by incorporating the analysis of phase randomization, thus improving the accuracy of the velocity computation. A device based on the invention is developed using a laser, an imager to record and process the speckle information, a display unit, and a data storage unit. Since the image of the sampled area and the speckle data can be collected using a common aperture system, the magnification factor and the image size will be the same, eliminating registration errors due to these factors. The computed blood velocity map can be superimposed onto a digitized image of the sampled area for easy visualization. Motion artifacts due to slight motions of the sampled tissue and the device reduce the signal-to-noise ratio of both LDV and LSCA methods. The LDV method reduces the effects of motion artifacts by filtering out low frequency (<30 Hz) signals, whereas this invention applies fast exposures to reduce these effects.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
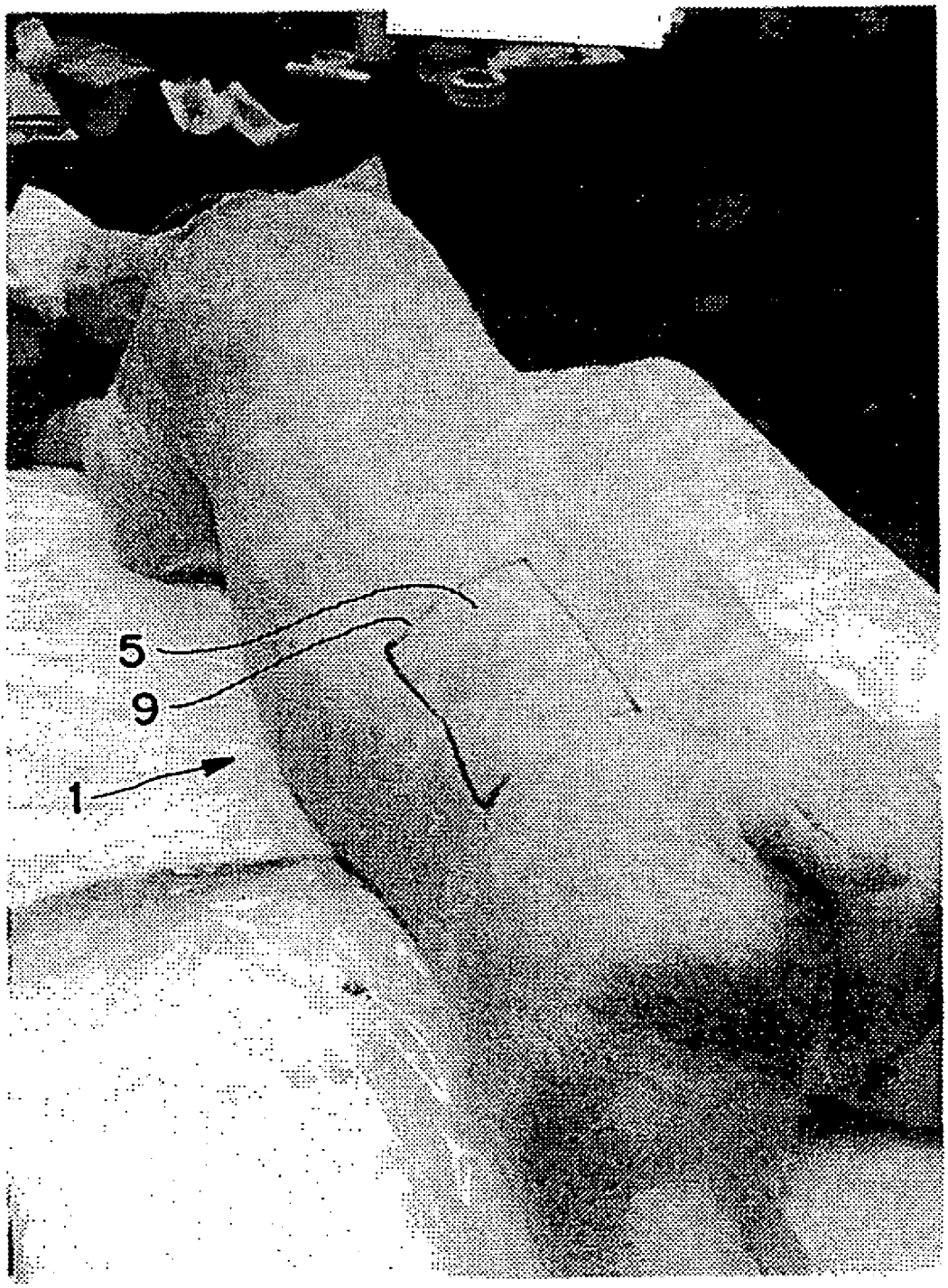
FIG. 1 is a photograph of a pig having a dorsal flap.

The LSCA/MS device consists of a laser system for illuminating the sampled tissue, a collection system for collecting tissue images and laser speckle data from tissue, a data processing system, and a display system.

The laser system consists of a laser and a beam expanding telescope that consists of a focusing lens and a pinhole to illuminate the sampled area with a uniform beam.

The collection system consists of a laser filter, a multi-element collection lens, a shutter, and a detector unit. The laser filter is used to eliminate the ambient light from laser speckle images. A visual tissue image can be obtained by removing the laser filter. The multi-element lens is used to collect the scattered light and to focus an image onto a detector array. The shutter is used to control the exposure (integration) time.

The data processing unit initializes the device by setting the exposure time, coordinates the timing for collecting speckle images with the blood pulse of the patient, interrogates the detector array to collect data, processes the data to obtain blood velocities, archives the data, and displays an image of the blood velocity map.

Optically, the major difference between blood velocity measurements for skin, breasts, flaps, underlying tissue, internal organs, retinas, etc., is the magnification factor of the optical system. The linear magnification of the systems for monitoring skin flap and breast tissue is about 0.05 (i.e., imaging an object of the size 20 cm×20 cm onto a detector with a 1-cm$^2$ sensing area). The linear magnification is about 3.3 if using the invention to measure human retinal blood velocities (i.e., imaging the retina of the size of about 3 mm×3 mm onto a 1-cm$^2$ sensing area). The optical system of the invention can be designed to accommodate various magnifications. Using a detector array with a 1-cm$^2$ sensing area and 1024×1024 pixel elements, a 20-μm spatial resolution can be achieved with a 7-pixel×7-pixel computation neighborhood.

The images can be viewed during alignment and data collection. They can be collected with different integration (i.e., exposure) times to facilitate better quantification of the differences in blood velocities. Output of the detector can be collected by a frame grabber in a computer. The frame grabber uses direct memory access where the image data are written directly to the hard drive, allowing fast acquisition of sequential images. The system can be visually aligned by viewing the images on a display monitor. Data are collected as uncompressed files, since image compression schemes generally result in the loss of image quality.

The invention provides multiple scattering algorithms for relating speckle contrast to characteristic blood velocity. Multiple scattering effects are generally ignored by researchers who apply coherent optical techniques to the measurements of blood velocity. In the case of retinal blood velocity measurements, computations based on single scattering analysis are acceptable since the retinal vascular structures are very close to the surface. However, single scattering algorithms fail in regions of high reflectivity, such as the optical nerve head.

The configuration of the invention can be varied to suit the needs of different applications.

Figure 6:
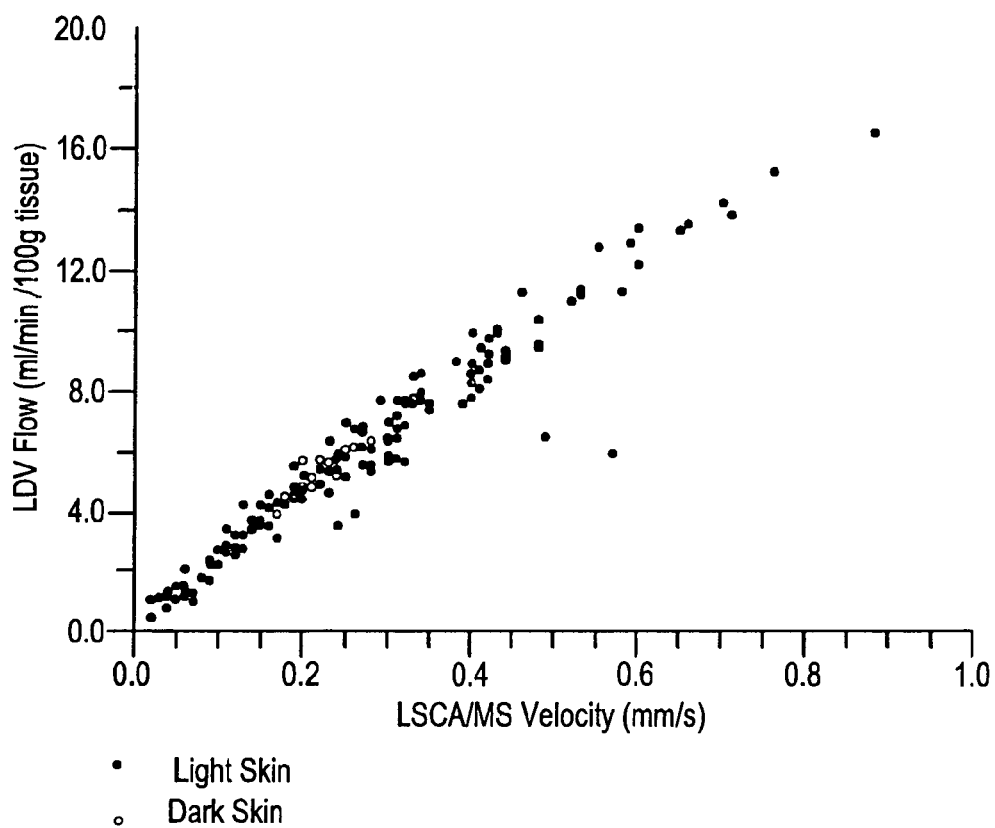
FIG. 6 is a comparison of the characteristic blood velocity obtained with the techniques described in the invention with prior art LDV flow readings.

In one example, measurements of skin blood velocity on juvenile pigs were performed to demonstrate the method. The skin of pigs most closely models the response of human skin, regarding its physiological and biochemical properties as well as its vascular supply. The LDV and LSCA/MS techniques were performed on the animals. The LDV device consists of two fibers embedded in a 1-cm diameter disk. Consequently, registering the LDV and LSCA/MS measurements exactly is not possible. Measurements were obtained at points on and near the sites where epigastric and dorsal flaps would be cut and elevated. Measurements on the flaps were made both before and after incision and elevation, and after the flap was severed. Data were also collected on exposed muscle tissue. The comparison of data is shown in FIG. 6.

Figure 7:
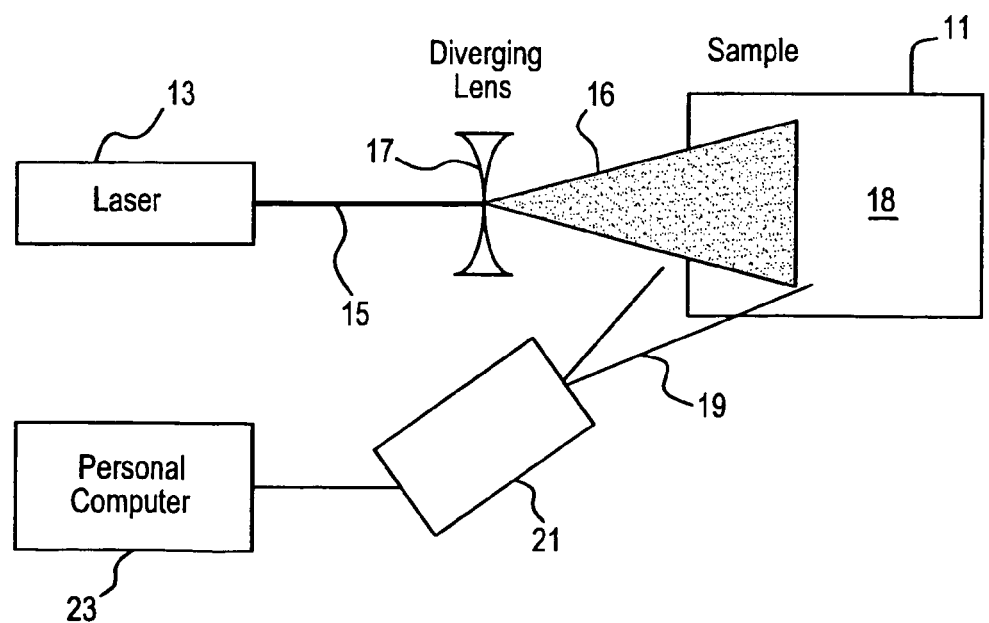
FIG. 7 schematically shows a basic measurement apparatus.

A block diagram of the preliminary experimental design is shown in FIG. 7. The beam 15 from an 8-mw continuous-wave diode laser 13 operating at 670 nm was expanded using a diverging lens 17. The tissue 11 was illuminated with the expanded beam 16 to cover an area 18 of about 10 cm$^2$, resulting in a power density of $3.0\times10^{-4}$ W cm$^{-2}$, which is much less than the maximum permissible exposure (MPE) for human skin (0.2 W cm$^{-2}$) at 670 nm (Chapter 21, Federal Code of Regulations; American National Standards Institute, ANSI Z136.1-1994). The laser speckle image 19 is collected with a collection system 21 consisting of a focusing lens, a shutter, and a detector array. The shutter and the detector array are operated under the control of a personal computer 23 (PC). The speckle pattern formed by light scattered by tissue is constant and serves as the background. The pattern formed by RBCs is dynamic and cannot be observed with human eyes. The raw data are downloaded from the detector to PC 23. The data are decoded to retrieve color information for each pixel. The average intensity and the standard deviation in each 7-pixel×7-pixel square neighborhood were computed and their values assigned to the central pixel of the square array. This process is repeated for every pixel. Speckle contrast of each pixel is computed using Eq. (3). The data can be plotted using a 3D plotting program or as a false-color image superimposed on the original image.

Measurements were made on a porcine 1 random dorsal flap 5 shown in FIG. 1 that was cut, elevated, and then sewn back in position. The underlying muscle 9 was visible at the edges of the flap. Both the laser Doppler and the LSCA/MS measurements were obtained at the tip, midpoint, and base of the flap. Blood velocity varies from high levels seen in the underlying muscle to near-normal (equivalent to those obtained prior to cutting and elevating the flap) at the base of the flap to much lower values at the tip of the flap. The distal end of the flap was visibly ischemic during measurements. After measuring the blood velocity in the flap, the flap was moved away to expose the underlying muscle layer.

Figure 2:
FIG. 2 shows a gray scale blood velocity map of a pig with a dorsal flap sutured in position along three edges. The higher blood velocities in the underlying muscle layer are visible at the edges of the flap.

FIG. 2 shows a representative gray scale blood velocity map superimposed on the image 3 of the flap 5 after it had been sewn into position at seven locations 7. High blood velocities in the underlying muscle layer 9 can be seen at the edges of the flap, indicated by brighter gray levels.

FIG. 6 shows a comparison of the blood flow data obtained with the LDV method and the characteristic blood velocity $V_c$ obtained from speckle images. The LDV time constant was set to 10 sec (as compared with the LSCA/MS exposure time of 2 ms). Since the LDV measurements were position sensitive, a series of three LDV readings were obtained at each position. The figure shows a good correlation between the LDV method and the invention, considering that the LDV method provides only point measurements. To increase cutaneous blood flow, the pig skin was treated with Iloprost dissolved in DMSO (dimethyl sulfoxide) to dilate the blood vessels. Both the LDV and the LSCA/MS data from measurements of Iloprost-treated skin of the pig show increased cutaneous blood velocities, with the increase ranging from a factor of 2.2 to 4.5.

Figure 3:
FIG. 3 shows a gray scale blood velocity map of an exposed muscle layer of a pig.

FIG. 3 shows a gray scale blood velocity map 25 of the flap superimposed on the laser speckle image 24 of the muscle layer 9.

Figure 4:
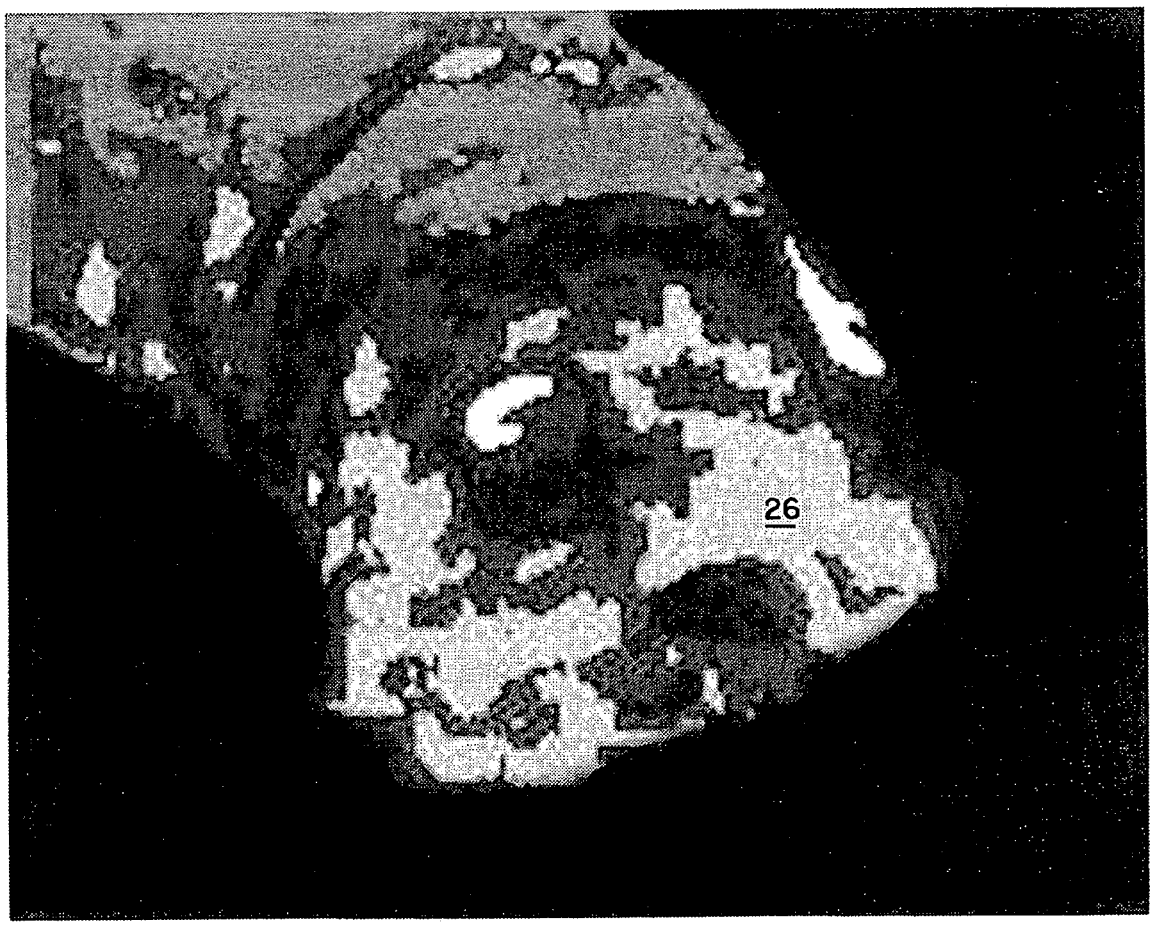
FIG. 4 shows a gray scale blood velocity map of a skin surface, in this case a pig's nose.

FIG. 4 shows a gray scale blood velocity map 27 of the nose 26 of a pig.

Figure 5:
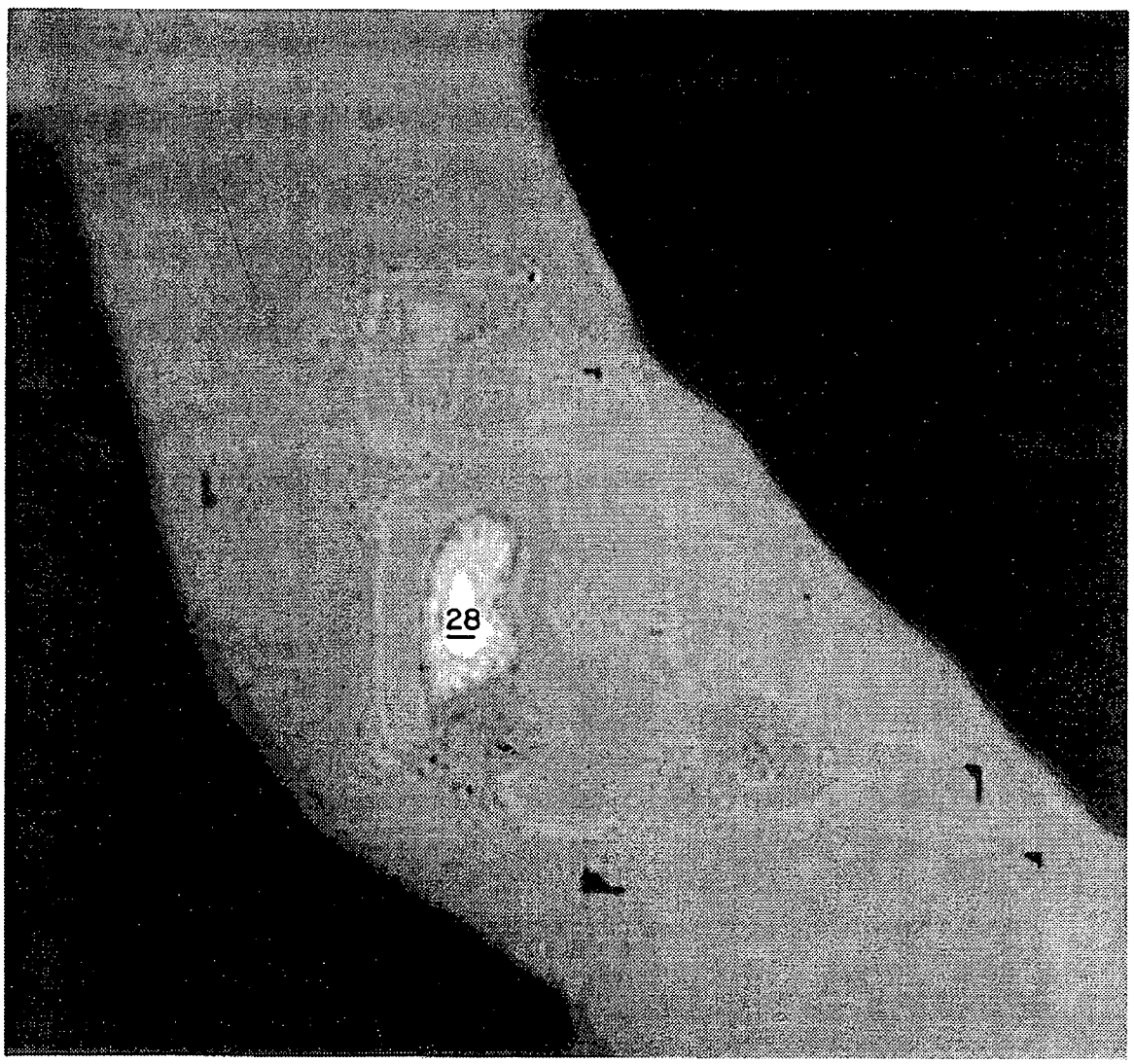
FIG. 5 shows a gray scale blood velocity map of a human arm where a small area had been exposed to Iloprost, a vasodilating agent.

FIG. 5 shows a gray scale blood velocity map 29 of a human arm where a small area 28 had been exposed to Iloprost, a vasodilating agent.

The invention provides real-time measurements for quantitative monitoring of tissue perfusion. The electronics of the device can be specially designed to control operation parameters such as the exposure time, field stop (depth of field), focusing of the lens, image exposure sequencing, image resolution, magnification, and the ability to access the raw data.

Figure 8:
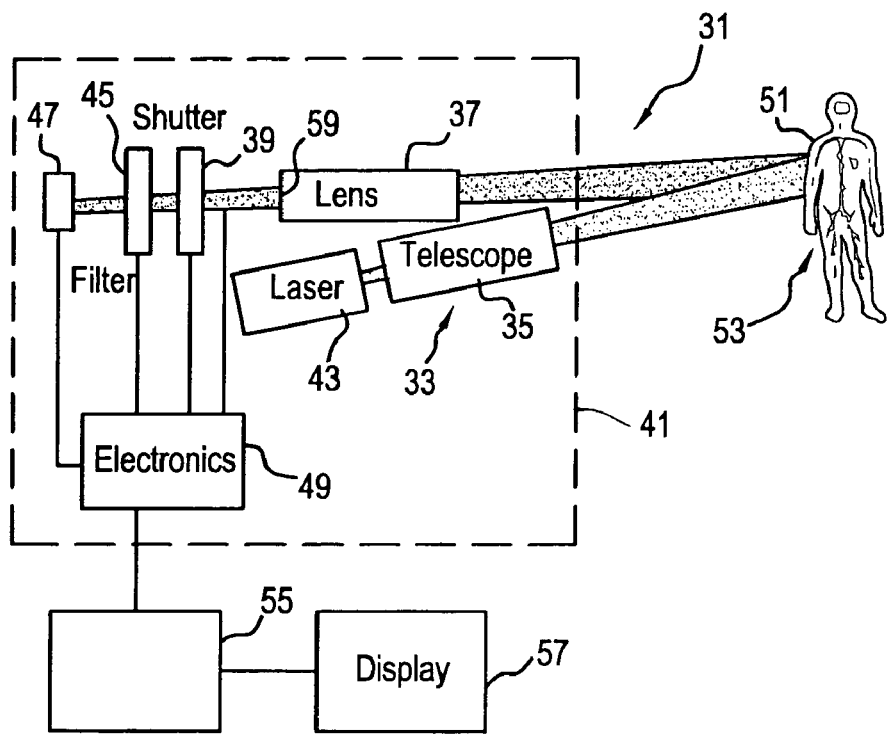
FIG. 8 schematically shows elements of an LSCA/MS system.

Any imaging device based on an array that allows independent intensity measurement at each pixel can be used as the LSCA/MS detector. A more advanced device 31 shown in FIG. 8 provides for laser speckle measurements of tissue. Multi-element optical systems 33 are used for both the beam expanding system such as a telescope 35 and the collection system such as a lens 37, enabling the operator to control the size of illumination on tissue and the magnification of the image on the detector array.

The advanced device shown in FIG. 8 has a single unit 41 that houses a He—Ne laser 43, a beam expanding telescope 35, a collection lens 37, a shutter 39, a filter 45, a detector array 47, and control electronics 49. Due to its higher beam quality than that of diode lasers, the He—Ne laser 43 is selected as the source. It operates in the $TEM_{00}$ mode, producing output beams with well-defined Gaussian cross-section. The laser output is expanded to illuminate the tissue 51 on the body 53.

The imaging device uses a detector array as the detector. A laser filter 45 is used to shield the detector array 47 from ambient light. The multi-element lens 37 collects light reflected and scattered from the tissue and matches the size of the image to the detector array, maximizing resolution. A shutter 39 is used to control the exposure time. A field stop 59, internal to the multi-element lens unit, allows spatial filtering of the image to obtain a desired depth of field for focusing the illuminated tissue. It also eliminates most of the room light from entering the detector. Specially designed electronics control the operation of the detector array and the shutter.

The detector operates in two modes:
(1) A semi-continuous mode (~5 frames/sec) for alignment purposes. The detector array is interrogated by the computer 55 after each frame, and the image is displayed on the monitor 57.
(2) A single frame mode. After closing the shutter and flushing the detector to restore the baseline, the shutter is again opened for the desired exposure duration and closed. The detector array 47 is interrogated and the image displayed. The image data are processed to obtain blood velocities.

To reduce measurement variability caused by the pulsatile nature of blood flow, data collection can be triggered during diastole by means of a signal indicating the cardiac cycle to ensure that the measurements occur at the same point in the arterial pulse. The trigger signal can be introduced as a signal from a piezoelectric blood pressure transducer or an optical arterial blood pulse sensor mounted on a fingertip or an ear clip secured on one of the ears.

The image scene is viewed during alignment and data acquisition. Images are collected with different integration (exposure) times for better quantifying differences in blood velocities. The optical system is housed in a rigid case 41 mounted on a tripod and is connected to a PC 55. The operator can visually align the system using the laser and view detector images on the monitor 57. The data collected are uncompressed, since image compression schemes usually results in loss of image information. The data analysis algorithms allow deeper mappings of the tissue.

Either a black and white or a color detector system can be used. One advantage of using color detectors is the ease of alignment in the semi-continuous mode. A red spot (if a HeNe laser is used) on the skin is more readily visible in a color image than a bright spot in a black and white image. However, monochrome detectors are less expensive and more sensitive (usually an order of magnitude) than color detectors.

The chosen array must have sufficient accuracy to detect spatial variations with millimeter resolutions. The spatial resolution depends on the number of elements in the array and the optical system used to form the image. For measuring blood velocity, the sensitivity of the detector must be such that the image can be collected within a desired period, such as 1 ms.

Figure 11:
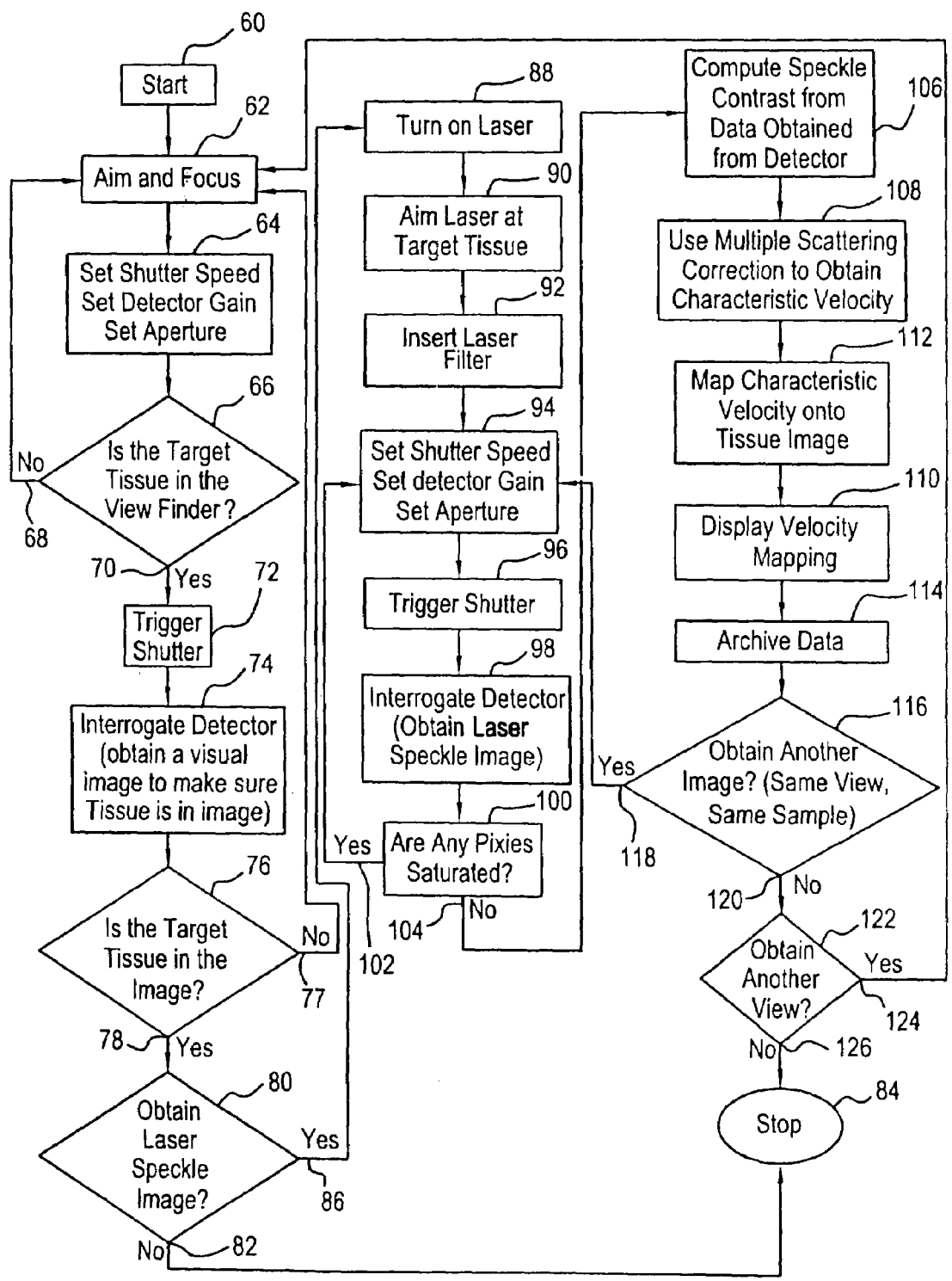
FIG. 11 is a schematic representation of steps for obtaining blood velocity values.

FIG. 11 generally shows operation of the system.

The system is started 60 and aimed and focused 62. The shutter speed, detector gain and aperture are separately set 64. A decision is made 66 to see if the target tissue is in the view finder. If the answer is no 68, a return to the aim and focus step 62 is required. If the answer is yes 70, the trigger shutter 72 is tripped, and the PC interrogates the detector to obtain a visual image 74. A decision is made 76 to see if the visual image contains the targeted tissue. If the answer is no 77, a return to step 62 is required. If the answer is yes 78, the system decides whether to obtain a laser speckle image 80. If a laser speckle image is not desired 82, the system is stopped 84.

If a laser speckle image is to be obtained 86, the laser is turned on 88, and the laser is aimed 90 at the target tissue. A laser filter 92 is inserted. The shutter speed, detector gain and aperture are set 94, and the shutter is triggered 96. The detector is interrogated 98 to obtain a laser speckle image, and it is determined 100 if there are any saturated pixels. If saturated pixels exist 102, the system returns to adjust the shutter speed, detector gain and/or aperture 94. If there are no saturated pixels 104, speckle contrast is computed 106 from the data obtained from the detector. The system uses multiple scattering correction to obtain characteristic velocity 108. It maps the characteristic velocity onto the image of the tissue 112, displays the velocity mapping 110, then archives the data 114. An inquiry is made whether it is desired to obtain another image 116 of the same view from the same sample. If the answer is yes 118, the system returns to step 94 and sets the shutter speed, detector gain and aperture for another image. If it is not desired to obtain another image 120, a decision is made 122 whether to obtain a different view. If the answer is yes 124, the system returns to the aim and focus step 62. If the answer is no 126, the system stops 84.

The software can be used to control system operations including data acquisition, analysis, and presentation.

The LSCA/MS device has different elements including the detector array, shutter, field stop, and electronics. These elements are controlled precisely to optimize the measurement accuracy.

To collect an image, the software sets the field stop, opens the shutter, sets and then counts down the exposure time, closes the shutter, and transfers the data from the detector to the computer. The sequence is repeated, and if necessary certain operating parameters are adjusted to obtain higher quality images. The system operation software determines the sequence of events and the timing of each sequence. The software provides for viewing the scene in near real-time. This is useful when aiming and adjusting the device, setting the size of the illuminated area with the beam expander, and optimizing the magnification of the image.

The invention can be used as an imager or a point detector. As a point detector, it allows the use of one pixel to determine the coherence parameter from an analysis of the autocorrelation function.

The data acquisition software includes software for operating the optical and electronic systems of the device, retrieving and storing the image, and recording relevant parameters such as image number, exposure setting, etc., in a log file.

For data analysis, any pixel size can be used to compute the mean and standard deviation of the characteristic velocity to optimize the viewing of speckle images at different magnifications.

The relation between speckle contrast and the characteristic blood velocity depends on the exposure time. Since the entire range of speckle contrast (from 0.0 to 1.0) can be observed with any exposure setting, in theory, one should be able to compute the characteristic blood velocity from speckle contrast at any exposure. The uncertainty in the determination of characteristic velocity is dependent on both speckle contrast and exposure time. Speckle contrast obtained from single exposure does not provide sufficient accuracy over a wide range (e.g., 0.05 to 5 mm/sec) of characteristic blood velocities. When a wide range of characteristic velocity is expected, accuracy can be improved by measuring speckle contrast at two or more exposure times. Longer exposures result in better accuracy for slower velocities and higher velocities are better determined with shorter exposure times.

Figure 9:
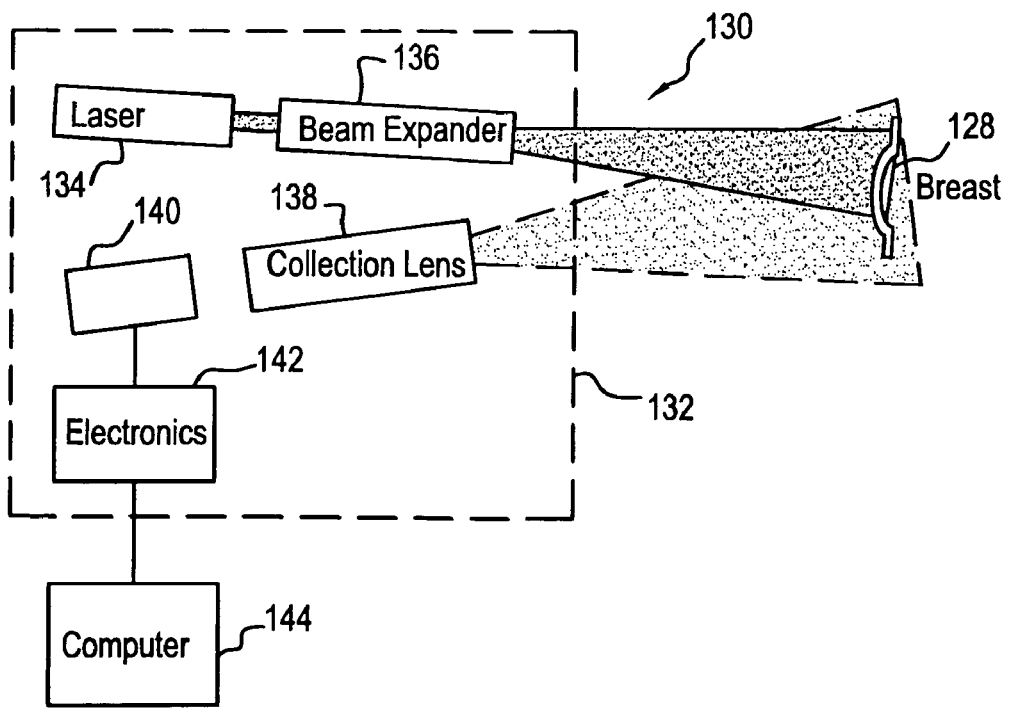
FIG. 9 schematically shows a breast examination system for measuring blood velocities in breast tissue.

The invention can be used to identify high cutaneous blood flow due to increased vascularity associated with breast tumors. FIG. 9 shows a system for noncontact measurements of blood velocity in breast tissue. Any areas of the breast showing increased blood velocities may suggest surface angiogenesis related to an occurrence of surface or deep tissue changes suggestive of tumors. Early detection of breast tumors provides a better chance for breast conservation treatment and increases survival rates.

For measuring three-dimensional objects, such as human breasts 128, a system 130 such as that shown in FIG. 9 can be used for blood velocity measurements. A single unit 132 houses a light source such as a HeNe laser 134, a beam expanding system such as a telescope 136, a collection system such as a multi-element lens 138, a detector such as an array 140, and control electronics 142 controlled by a computer 144. The laser output is expanded to illuminate the breast tissue 128. A laser filter can be used to shield the detector array 140 from ambient light. The multi-element lens 136 collects light reflected and scattered from the breast 128. The collecting lens matches the size of the breast image to the detector array, maximizing spatial resolution. The shutter exposes the detector array to the scattered light for a certain exposure time. The field stop spatially filters the image to obtain a certain depth of field. It also eliminates most of the ambient light from entering the detector. The detector and the shutter are controlled by the computer. The field stop, internal to the multi-element lens, is used to adjust the image=s depth of field.

Figure 10:
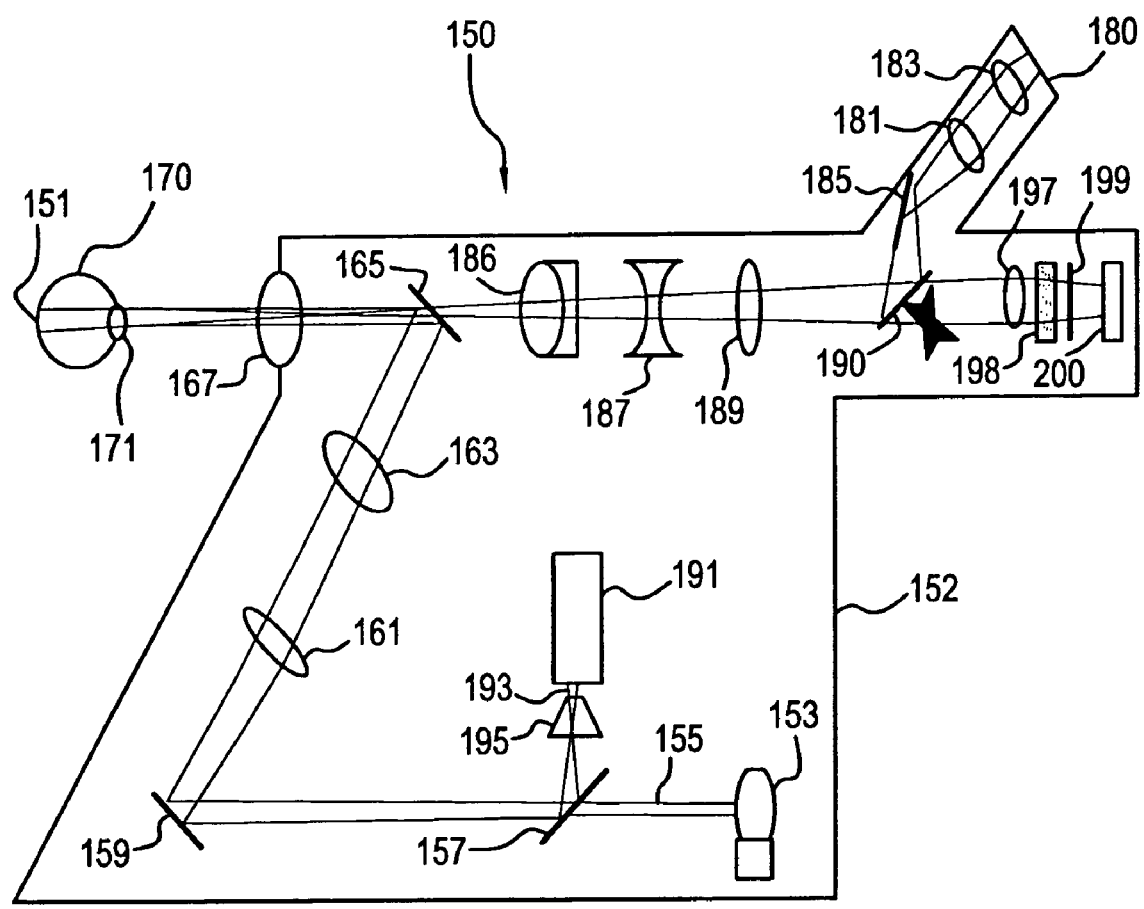
FIG. 10 is a schematic representation of a modified LSCA/MS optical system for aligning and sensing laser speckle in a small targeted area such as the retina.

Another important application of the invention is in the area of retinal blood flow monitoring. One of the most difficult challenges in ophthalmology is devising a noninvasive and quantitative method for evaluating retinal hemodynamics. Both the laser Doppler and the laser speckle point measurement methods have been used to detect the movement of RBCs in the order of the light wavelength. This invention provides a new and promising approach for imaging the retina with a unique laser speckle technique to retrieve retinal blood velocity information. Due to its small size and its location inside the eye, monitoring retinal blood velocity presents a technical challenge. FIG. 10 shows an example of a LSCA/MS device for measuring retinal blood velocity. It can be modified for use with endoscopes for blood velocity measurements of internal tissue. The system 150 is based on the design 152 of a slit lamp or a fundus camera for the determination of blood velocity in the retina 151. The system uses two light sources, a lamp 153 and a laser 191. By using the lamp, a full-color scene can be observed. The laser is used for monochromatic images and blood velocity measurements. There are four possible alignment approaches. They differ by the choice of the light source (lamp or laser) and the viewing method (eyepiece or video).

(1) Lamp Source, Eyepiece Viewing

A lamp 153 emits a light beam 155 that is transmitted by a partially transmitting mirror 157. The transmitted beam through mirror 157 impinges on mirror 159 and is reflected. The beam is then formed by lenses 161 and 163, and impinges onto the second partially transmitting mirror 165. Part of the beam is reflected from mirror 165, passes through lens 167, and impinges onto the target eye 170. The position and size of the light spot on retina 151 can be set by either adjusting the lens 167 or moving the eye 170 with respect to the device 150.

The beam then passes through the cornea 171, the enlarged pupil, the aqueous humor in the anterior chamber, the lens, and the vitreous humor in the posterior chamber, and impinges onto the retina 151. The light scattered by retina is collected by lens 167. It passes through the mirror 165 and is formed by lenses 186, 187 and 189.

When the movable mirror 190 is placed into the beam path, the light is reflected off the mirror 190 into an eyepiece 180. The eyepiece consists of a mirror 185 and lenses 181 and 183. The operator aligns the system 150 using the eyepiece 180.

When it is determined that the desired location and size of the light spot are on the retina 151, the lamp 153 is turned off, moveable mirror 190 is retracted, and the laser 191 is turned on. The laser beam 193 is expanded by a beam expander 195, reflected by mirrors 157 and 159, shaped by lenses 161 and 163, reflected from the mirror 165, and passes through lens 167 into the eye 170, and onto the retina 151.

The light scattered by the retina is collected by lens 167. It passes through mirror 165, is formed by lenses 186, 187, and 189, passes through a lens 197, a filter 198, and an open shutter 199 to illuminate the detector array 200. The laser filter 198 shields the detector array 200 from ambient light. The shutter 199, when open, exposes the detector array to scattered light for a predefined exposure time. The shutter can be coordinated with the on/off operation of the laser. A field stop can be added to filter the image to obtain a certain depth of field needed for retinal mapping.

(2) Lamp Source, Video Viewing

The lamp 153 emits a light beam that follows the path described previously until the element 189. For viewing the video image, the moveable mirror 190 is retracted. The scattered light passes through lens 197, laser filter 198, shutter 199, and impinges onto the detector 200. The video image is viewed on the display enabling the operator to observe the location and size of the light spot on the retina 151 and to align the system. The location and size of the light spot on retina can be adjusted as previously. When it is determined that the desired location and size of the light spot are on the retina 151, the lamp 153 is turned off, the laser 191 is turned on, and the speckle image can be obtained.

(3) Laser Source, Eyepiece Viewing

A laser 191 emits a light beam that is expanded by a beam expander 195 and reflected by a partially transmitting mirror 157. The beam is then reflected from mirror 159 and follows the path described previously until it is reflected into the eyepiece by mirror 190. The operator aligns the system using the eyepiece 180. When the desired location and size of the light spot are on the retina 151, the mirror 190 is retracted allowing acquisition of the speckle images.

(4) Laser Source, Video Viewing

The laser 191 emits a light beam that follows the path described previously until the element 189. For viewing the video image, the moveable mirror 190 is retracted allowing the operator to observe the location and size of the laser spot on the retina 151 and to align the system. After the alignment, speckle images can be obtained.

The duration of the exposure time and an optimum exposure time can be selected to maximize the information content of the image, i.e., to maximize the difference of the speckle contrast between the smallest and the largest expected characteristic velocities. As described previously, the system can operate in two modes: a semi-continuous mode for alignment purposes and a single-frame mode for collecting speckle image data.

While the invention has been described with reference to specific embodiments, modifications and variations of the invention may be constructed without departing from the scope of the invention, which is defined in the following claims.

We claim:

1. A method of measuring blood velocity in tissue, comprising the steps of:
    illuminating a tissue surface with laser energy;
    reflecting laser energy from the tissue surface and from near surface levels of the tissue;
    receiving the reflected and scattered laser energy on a detector array;
    detecting spatial distribution of speckle pattern of the reflected and scattered laser energy;
    analyzing the detected energy for laser energy scattering;
    computing the effects of multiple scattering induced by the movements of red blood cells and incorporating multiple scattering effects into the analysis of laser speckle statistics, and;
    evaluating the laser speckle to obtain a function of blood velocity distribution;
    and thereby determining blood velocity and perfusion, and viability of tissue in skin flaps, grafts and organs.

2. The method of claim 1, further comprising assessing blood perfusion in tissue according to the step of evaluating.

3. The method of claim 1, further comprising assessing tissue viability according to the step of evaluating.

4. The method of claim 1, further comprising assessing cutaneous blood velocities according to the step of evaluating.

5. The method of claim 1, further comprising assessing blood velocities in surgically exposed tissues according to the step of evaluating.

6. The method of claim 1, further comprising assessing internal blood velocities by internally or surgically introducing scopes having optical fibers, conducting the laser energy through optical fibers from proximal ends to distal ends thereof for the illuminating of the tissue surface and conducting the reflected and scattered laser energy through optical fibers to the detector array.

7. The method of claim 1, further comprising assessing angiogenesis within tissue according to the step of evaluating.

8. The method of claim 7, wherein the illuminating step comprises illuminating cutaneous tissue of a breast, and further comprising predicting presence of abnormal blood flow within the breast according to the assessing of angiogenesis.

9. The method of claim 1, wherein the illuminating step comprises illuminating a retina, and further comprising assessing retinal blood circulation according to the step of evaluating.

10. The method of claim 1, further comprising determining characteristic blood velocities in capillaries within the tissue according to the step of evaluating.

11. Apparatus for determining blood velocities in tissues, comprising:
    a laser for producing a laser beam;
    a beam expander in optical alignment with the laser for expanding the laser beam for illuminating an area of a tissue with the laser beam;
    a receiver for receiving reflected and scattered laser energy from the tissue;
    the receiver having a detector array, for detecting spatial distribution of speckle pattern of surface reflection and scattering of the laser energy from the tissue;
    an analyzer connected to the detector array for analyzing laser speckle related to red blood cell velocities in the illuminated tissue area; and
    wherein the analyzer analyzes spatial distribution of speckle intensity.

12. The apparatus of claim 11, wherein the receiver further comprises a collection system comprising a multi-element lens positioned between the tissue and the detector array for directing the reflected and scattered laser energy from the tissue surface to the detector array.

13. The apparatus of claim 12, further comprising an endoscope having, transmitting and receiving optical fibers having proximal and distal ends, wherein the laser is aligned with proximal ends of the transmitting fibers for introducing the laser beam into the fibers and for illuminating internal tissues with the laser energy, wherein distal ends of the receiving fibers receive surface reflected and scattered laser energy from the internal tissues, and wherein proximal ends of the receiving fibers are optically aligned with detectors in the detector array.

14. The apparatus of claim 11, further comprising a shutter between the detector array and the tissue for controlling the time of exposure of the detector array to the reflected and scattered laser energy from the tissue.

15. The apparatus of claim 11, further comprising a system for aligning the beam expander and the receiver with the sampled area.

16. The apparatus of claim 11, further comprising a frame for mounting the laser, the beam expander and the receiver in optical alignment with the tissue, and wherein the analyzer comprises a processor for performing laser speckle contrast analysis incorporating multiple scattering.

17. The apparatus of claim 16, wherein the frame is configured for mounting adjacent to a breast to illuminate an area of the breast and to receive laser energy reflected and scattered from the breast tissue.

18. The apparatus of claim 16, wherein the frame is configured for mounting close to an eye in optical alignment with a pupil and retina of an eye for illuminating the retina with the laser beam, and for receiving the laser energy reflected and scattered from the retina.

19. The apparatus of claim 16, wherein the frame is configured for mounting on a distal end of an endoscope for transmitting the laser beam through the endoscope to internal tissue, and for receiving reflected and scattered laser energy from the internal tissue through the endoscope.

20. The apparatus of claim 11, wherein the laser is a He—Ne laser.

21. Apparatus for assessing blood velocities in tissues, comprising:
a mount;
a laser on the mount for producing a laser beam;
a beam expanding system such as a lens on the mount in optical alignment with the laser for expanding the laser beam and for directing the laser beam to a tissue to be examined for blood velocities;
a receiver on the mount for receiving reflected and scattered laser energy from the tissue;
the receiver having a laser filter for blocking entry of ambient light;
a field stop in optical alignment with a detector for controlling the depth of field of receiving the reflected and scattered laser energy from the tissue;
a shutter in optical alignment with the field stop for controlling the length of time for receiving reflected and scattered laser energy from the tissue;
a detector comprising an array, in optical alignment with the field stop, the filter, and the shutter for detecting spatial distribution of speckle pattern of reflected and scattered laser energy;
a light collecting system such as a multiple-element collecting lens in optical alignment with the filter, the field stop, and the shutter for collecting reflected and scattered laser energy from the tissue and matching the size of the image to the detector array.

22. The apparatus of claim 21, wherein the beam expander is configured for illuminating an area of the breast with the laser beam, the collecting system is configured for matching the size of a breast image to the detector array, and the field stop is configured for obtaining a desired depth of field.

23. The apparatus of claim 21, further comprising a processor connected to the detector array for analyzing laser speckle.

24. A method of determining blood velocity in tissue, comprising:
turning on a laser;
setting shutter speed, detector gain, and aperture;
triggering a shutter;
interrogating a detector;
obtaining a laser speckle image from the detector; and computing speckle contrast from a spatial distribution of speckle pattern of the laser speckle image data obtained from the detector;
and determining blood velocity and perfusion and viability of tissue in skin flaps, grafts and organs.

25. The method of claim 24, further comprising initially:
aiming and illuminating target tissue;
focusing the image;
setting shutter speed, detector gain, and aperture;
determining if target image is in view;
triggering the shutter;
interrogating the detector; and
verifying the tissue is in image.

26. A method of obtaining tissue blood velocity data comprising:
turning on a laser;
aiming the laser at a tissue surface;
setting shutter speed;
setting detector gain;
setting aperture;
triggering a shutter;
interrogating a detector;
obtaining a laser speckle image;
determining if any pixels in the image are saturated;
when pixels are saturated, resetting shutter speed, detector gain, and aperture;
triggering the shutter;
interrogating the detector;
obtaining detector data;
obtaining a laser speckle image;
determining if pixels in the image are saturated;
if no pixels are saturated, computing speckle contrast from a spatial distribution of speckle pattern of the laser speckle image obtained from the detector data;
using multiple scattering correction;
obtaining characteristic velocity;
mapping the characteristic velocity on the visual image;
displaying the velocity mapping; and
archiving data;
and determining blood velocity and perfusion, and viability of tissue in skin flaps, grafts and organs.

27. The method of claim 26, further comprising initially:
aiming and focusing a light source on a tissue surface;
setting shutter speed;
setting detector gain;
setting aperture;
observing the tissue surface for correct aiming and focusing;
triggering the shutter;
interrogating the detector; and
obtaining a visual image to make sure the tissue surface is in the image.

28. A method of measuring blood velocities in tissues comprising:
opening a shutter;
illuminating an area of a tissue with a laser for a predetermined exposure time;
concurrently receiving reflected and scattered laser energy from the tissue;
detecting spatial distribution of speckle pattern of the laser energy with a detector array;
closing the shutter;
examining spatial distribution of intensity fluctuation time averaged over the exposure time; and
determining blood velocities and perfusion in the tissue and viability of the tissue according to the time averaged spatial distribution of intensity fluctuation.

29. The method of claim 28, wherein the illuminating process comprises opening and closing a shutter between the laser and the tissue.

30. The method of claim 28, further comprising providing single exposure laser photography and using spatial averaging of the temporal measurements.

* * * * *